United States Patent [19]

Hitzel et al.

[11] Patent Number: 4,542,127
[45] Date of Patent: Sep. 17, 1985

[54] ANTIDIABETIC SALICYLIC ACID DERIVATIVES

[75] Inventors: Volker Hitzel, Hofheim am Taunus; Rudi Weyer, Kelkheim; Karl Geisen, Frankfurt am Main; Harald Ritzel, Mainz, all of Fed. Rep. of Germany

[73] Assignee: Hoechst Aktiengesellschaft, Fed. Rep. of Germany

[21] Appl. No.: 479,906

[22] Filed: Mar. 29, 1983

[30] Foreign Application Priority Data

Mar. 31, 1982 [DE] Fed. Rep. of Germany ....... 3211934

[51] Int. Cl.$^4$ .................. A61K 31/625; C07D 401/04
[52] U.S. Cl. .................. 514/161; 260/244.4; 546/112; 546/125; 546/126; 546/133; 546/138; 546/144; 546/169; 546/194; 546/272; 546/275; 546/281
[58] Field of Search ............... 546/275, 281, 194, 272, 546/125, 133, 138, 144; 424/266, 232, 265; 260/244.4

[56] References Cited

U.S. PATENT DOCUMENTS 4,181,658  1/1980  Hitzel et al. ................... 424/266
4,221,815  9/1980  Weyer et al. .................. 424/319

FOREIGN PATENT DOCUMENTS 23569    2/1981  European Pat. Off. ........... 424/266
0056144  7/1982  European Pat. Off. ........... 424/266
2500157  7/1976  Fed. Rep. of Germany ...... 424/319
2706977  8/1978  Fed. Rep. of Germany ...... 424/266
1080705  8/1967  United Kingdom ................ 424/322

OTHER PUBLICATIONS

Chemical Abstracts, 95:115322k (1981) [Evr. Pat. Appl. 23,569, 02/11/81].

Primary Examiner—Richard A. Schwartz
Attorney, Agent, or Firm—Finnegan, Henderson, Farabow, Garrett & Dunner

[57] ABSTRACT

Salicylic acid derivatives of the formula I

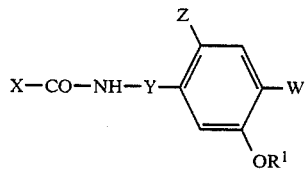

wherein $R^1$, W, X, Y and Z have the meanings indicated or a physiologically tolerated salt thereof, processes for their preparation, pharmaceutical formulations based on these compounds and their use as antidiabetic agents.

4 Claims, No Drawings

ANTIDIABETIC SALICYLIC ACID DERIVATIVES

The invention relates to salicylic acid derivatives of the general formula I

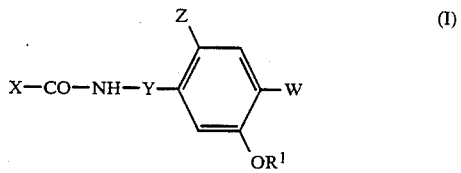

and their physiologically tolerated salts which are distinguished by a powerful hypoglycemic effect and thus can be used as medicaments.

In the general formula I,
W denotes a carboxyl group or an alkoxycarbonyl group having up to 4 carbon atoms in the alkoxy moiety
Z denotes a hydrogen atom or a halogen atom,
$R^1$ denotes a hydrogen atom, a ($C_1$-$C_6$)-alkyl group, a ($C_2$-$C_6$)-alkenyl group or an alkoxyalkyl group having a total of up to 6 C atoms,
Y denotes an alkylene radical having 1-3 C atoms
X denotes a pyridine radical of the formula II

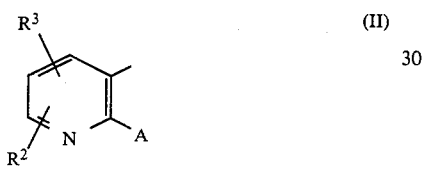

or a quinoline radical of the formula III

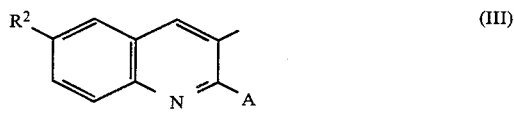

wherein
$R^2$ denotes a hydrogen atom or a halogen atom or an alkyl group having up to 4 C atoms or an alkoxy group having up to 4 C atoms in the alkoxy moiety,
$R^3$ denotes a hydrogen atom or an alkyl group having up to 4 C atoms
A denotes a ($C_4$ to $C_8$)-alkyleneimino group, which is unsubstituted or substituted by one or two ($C_1$-$C_4$)-alkyl groups, these groups being in each case bonded to the rest of the molecule via the nitrogen atom.

Examples of suitable salts for the case where W represents a carboxyl group are alkali metal and alkaline earth metal salts, preferably the sodium and potassium salts. Suitable acid addition salts with inorganic and organic acids are preferably the hydrochlorides.

In the above definition, halogen denotes chlorine and bromine, chlorine being preferred.

Y denotes in particular the —$CH_2$—$CH_2$ group and W denotes in particular the carboxyl or alkoxycarbonyl group having up to 2 carbon atoms in the alkoxy moiety. $R^1$ denotes preferably a $C_1$-$C_3$ alkyl group and $R^2$ and $R^3$ as well as Z denote preferably a hydrogen atom.

Alkyleneimino groups are to be understood to include cyclic amines, such as pyrrolidine, piperidine, hexamethyleneimine, heptamethyleneimine and octamethyleneimine. These can be substituted with one or two alkyl groups. Alkyl substituted piperidines are preferred, such as, for example, 3-methylpiperidine and 3,5-dimethylpiperidine.

The cyclic amines which are substituted by two alkyl groups are in general present in the form of cis-trans mixtures. However, they may alternatively be present in the form of the pure isomers. For reasons of simplicity these mixtures are not particularly referred to as cis-trans mixtures.

In addition, the invention relates to processes for the preparation of salicyclic acid derivatives of the formula I or a physiologically tolerated salt thereof pharmaceutical formulations which contain them or which are composed of them and their use for the treatment of diabetes.

The processes for the preparation of the salicylic acid derivatives of the formula I or a physiologically tolerated salt thereof comprise
(a) reacting an amino compound of the general formula IV

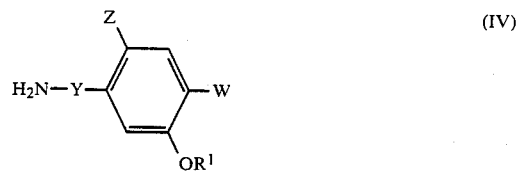

in which $R^1$, Y, Z and W have the abovementioned meanings, with a carboxylic acid or a reactive derivative of the carboxylic acid of the formula V, which can also be produced in the reaction mixture,

wherein X has the meanings indicated,
(b) reacting an amino compound of the general formula IV

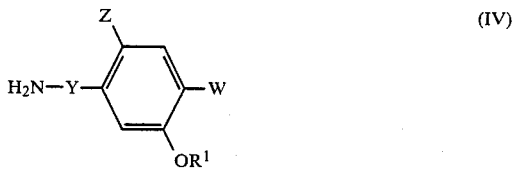

in which $R^1$, Y and Z have the abovementioned meanings and W represents an alkoxycarbonyl group having up to 4 C atoms in the alkoxy moiety, with a carboxylic acid or a reactive derivative of the carboxylic acid of the formula VI, which can also be produced in the reaction mixture,

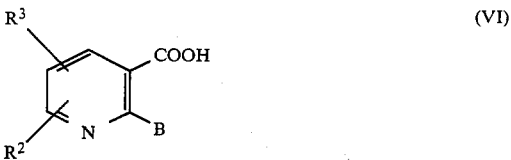

or with a carboxylic acid or a reactive derivative of the carboxylic acid of the formula VII, which can also be produced in the reaction mixture,

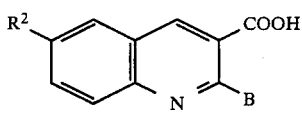

in which $R^2$ and $R^3$ have the meanings indicated for the formulae II and III and B represents a halogen atom, and then replacing the substituent B in the compounds thus obtained by A, (c) in a compound of the general formula VIII

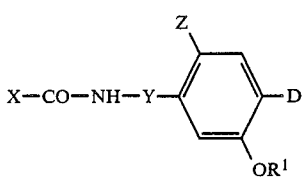

in which $R^1$, X, Z and Y have the abovementioned meanings and D denotes a group which can be converted by oxidation into a carboxyl group, oxidizing this group D to the COOH group (W=carboxyl) or (d) in a compound of the general formula IX

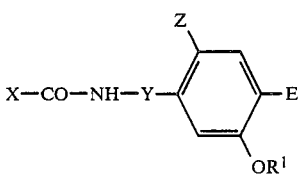

wherein $R^1$, X, Y and Z have the abovementioned meanings, and E represents a group which can be converted by hydrolysis into a carboxyl group, hydrolyzing the group E to the COOH group (W=carboxyl), and converting the compounds obtained by processes (a) to (d), if appropriate, by esterification or transesterification into esters (W=alkoxycarbonyl having up to 4 C atoms in the alkoxy moiety) or by hydrolysis into the free acids (W=carboxyl), or into physiologically tolerated salts with bases or acids.

Examples of suitable reactive derivatives for the carboxylic acids of the formula V, VI and VII used in processes a and b are the alkyl, aryl or aralkyl esters the imidazolides, the anhydrides, the mixed anhydrides with aliphatic or aromatic carboxylic or sulfonic acids and also carbonic acid esters, the N-acyloxyimides and the active esters.

Examples of reagents for the preparation of these reactive derivatives are acid-activating and/or water-removing reagents, such as esters of chloroformic acid, N,N-carbonyldiimidazole, N,N-dicyclohexylcarbodiimide or 1-hydroxybenzotriazole.

The reactions according to processes (a) and (b) are carried out in the presence of solvents.

The solvents which are preferably employed are chlorinated hydrocarbons such as methylene chloride or chloroform, tetrahydrofuran, toluene or dimethylformamide. For cases in which an acid-removing agent is necessary for the activation or acylation, inorganic or organic bases are added, such as, for example, sodium carbonate or triethylamine or pyridine. The reaction temperatures are between −10° C. and the boiling points of the solvents used.

Suitable oxidizable groups in the starting compounds VIII according to process (c) are for example the formyl or hydroxymethyl groups. The preferred oxidizing agent is manganese dioxide. The most suitable solvent is methylene chloride.

Examples of suitable E in the starting compounds IX for process (d) are the nitrile group, the substituted or unsubstituted amide group or the ester group.

The hydrolysis reaction is carried out with acids or bases in mixtures of water and alcohol at room temperature or at elevated temperatures.

If a compound of the general formula I, in which W denotes a carboxyl group, is obtained, this can be converted into an ester. The subsequent esterification is advantageously carried out by an acid-catalyzed reaction in the appropriate alcohol or by activation of the acid and reaction with the appropriate alcohol. If the reaction products are compounds wherein A is a cyclic amine substituted by two alkyl groups, the cis-trans mixtures obtained can be split up into the individual components by usual methods, for example by column chromatography. The compounds obtained can be converted into physiologically tolerated salts by reaction with bases or acids. When W represents a carboxyl group alkaline earth metal hydroxides, carbonates or bicarbonates or alkali metal hydroxides, carbonates or bicarbonates and also alkali metal alcoholates are particularly suitable for salt formation. Suitable acids for salt formation are inorganic acids, such as, for example, hydrochloric acid or sulfuric acid or organic acids, such as, for example, maleic acid or fumaric acid.

The embodiments of the processes according to the invention can, in general, be widely varied in respect of the reaction conditions.

The compounds according to the invention are distinguished by valuable pharmacological properties, in particular hypoglycemic properties. Thus they are suitable as medicaments, in particular as anti-diabetic agents.

The hypoglycemic activity of the compounds according to the invention is demonstrated, for example, by feeding them, as the free compounds or in the form of their salts, to rabbits receiving a normal diet and then finding the blood sugar value over a relatively long period by the known method of Hagedorn-Jensen or using an autoanalyzer. Routine determination of the hypoglycemic activity is carried out, for example, with doses of 10 mg or 2 mg or 0.4 mg of active substance per kg of experimental animal by known methods.

The compounds I to III according to the invention and shown below

I. Na salt of 2-ethoxy-4-(2-(2-(3,5-dimethylpiperidino)-pyridine-3-carboxamido)ethyl)benzoic acid II. Na salt of 4-(2-(2-(3,5-dimethylpiperidino)pyridine-3-carboxamido)ethyl)-2-methoxybenzoic acid III. Na salt of 4-(2-(2-(3,5-dimethylpiperidino)quinoline-3-carboxamido)ethyl)-2-methoxybenzoic acid were investigated in comparison with the compound IV described in the European Patent Application with publication No. 0,023,569

IV. 4-(2-(2-piperidinopyridine-3-carboxamido)ethyl)-benzoic acid.

The substances were each administered orally to rabbits at a dose of 2 mg/kg and the blood sugar values were determined over a relatively long period using an autoanalyzer. The table below shows the percentage decrease in blood sugar compared to the control after . . . hours:

| Substance | time (in hours) | | | |
|---|---|---|---|---|
| | 1 | 3 | 5 | 24 |
| I | −24 | −31 | −29 | −15 |
| II | −34 | −53 | −41 | −8* |
| III | −21 | −27 | −55 | +11 |
| IV | −13* | −4* | −4* | |

* = Not statistically significant

The properties of the compounds permit the use, in the therapy of diabetes mellitus, of doses which are so small that the formulation only normalizes the previously lowered response of the pancreas to an increased level of sugar in the blood.

The compounds described preferably serve for the preparation of formulations for the treatment of diabetes mellitus by oral administration. They are administered as such or in the form of a physiologically tolerated salt thereof, or in the presence of substances which lead to salt formation. The formulations can also contain other active compounds in addition to the substances according to the invention or a physiologically tolerated salt thereof. Suitable medical formulations are preferably tablets which, in addition to the compounds according to the invention or their salts, contain the customary excipients and auxiliaries, such as talc, starch, lactose or magnesium stearate. In this context, it can be advantageous to employ the active compound or compounds in a ground or finely precipitated forms or as a mixture of these forms. A formulation which contains the compounds according to the invention as the active compound, for example a tablet or a powder, with or without additives, is advantageously converted into a suitable dosage form. For this purpose, the dose selected is that adjusted to the effectiveness of the compound used and the desired effect. Advantageously, the dosage per unit is about 0.5 to 50 mg, preferably 1 to 20 mg, but dosage units can also be used which are larger or smaller than this and these should be divided or multiplied as required before administration.

The following examples show some of the numerous variants of the process which are suitable for synthesis of the compounds according to the invention. However, they are not intended to represent a restriction of the subject of the invention.

EXAMPLE 1

Na salt of 2-ethoxy-4-(2-<2-(3,5-dimethylpiperidino)pyridine-3-carboxamido>ethyl)benzoic acid 5.7 g of ethyl 2-ethoxy-4-(2-<2-chloro-pyridine-3-carboxamido>ethyl)benzoate in 100 ml of toluene with 6.8 g of 3,5-dimethylpiperidine were stirred under reflux for four hours. After cooling down, the mixture was concentrated in vacuo, the residue was taken up in water and ethyl acetate, the phases were separated and the aqueous phase was extracted a further two times. The combined ethyl acetate phases were evaporated and the residue was purified over a silica gel column with methylene chloride/ethyl acetate 5:1. The ethyl 2-ethoxy-4-(2-<2-(3,5-dimethylpiperidino)pyridine-3-carboxamido>-ethyl)benzoate was then hydrolyzed. 4.1 g of ester were boiled in 100 ml of ethanol and 25 ml of 2N sodium hydroxide solution for two hours. After cooling down, the ethanol was distilled off under reduced pressure and the aqueous solution was acidified with glacial acetic acid.

The aqueous phase was extracted with methylene chloride, and this was dried and evaporated. The remaining semi-solid residue was converted into the Na salt by dissolving in ethanol and addition of an equimolar amount of 1 N sodium hydroxide solution. After evaporation and trituration with a little ethanol, the Na salt of 2-ethoxy-4-(2-<2-(3,5-dimethylpiperidino)pyridine-3-carboxamido>ethyl)benzoic acid melted at 263°–266° C.

The ethyl 2-ethoxy-4-(2-<2-chloro-pyridine-3-carboxamido>ethyl)benzoate used as the starting material was prepared in the following manner: 2-hydroxy-4-methylbenzoic acid was reacted with $K_2CO_3$ and diethyl sulfate in acetone to give ethyl 2-ethoxy-4-methylbenzoate (boiling point at 1 mm=107°–108° C.), which was hydrolyzed to give the corresponding carboxylic acid (melting point 72°–74° C., from acetone). Subsequent bromination provided the 4-bromomethyl compound (melting point 98°–100° C.), which gave the 4-cyanomethyl compound (melting point 114°–117° C.) with sodium cyanide. Ethyl 2-ethoxy-4-(2-aminoethyl)-benzoate hydrochloride was obtained by catalytic hydrogenation with Raney nickel and reaction with ethanolic hydrochloric acid, and this was reacted with 2-chloronicotinic acid, methyl chloroformate and triethylamine to give ethyl 2-ethoxy-4-(2-<2-chloro-pyridine-3-carboxamido>ethyl)benzoate (melting point 83°–85° C. after column purification).

The following compounds were obtained in an analogous manner: Na salt of 2-ethoxy-4-(2-<2-heptamethyleneimino-pyridine-3-carboxamido>ethyl)benzoic acid.

Melting point 253°–255° C. (from ethanol).

Na salt of 2-ethoxy-4-(2-<2-(4-methylpiperidino)-pyridine-3-carboxamido>ethyl)benzoic acid.

Melting point 210°–213° C. (from acetone).

Na salt of 2-ethoxy-4-(2-<2-(3-methylpiperidino)-pyridine-3-carboxamido>ethyl)benzoic acid.

Melting point 217°–220° C. (from ethanol/ether).

Na salt of 2-ethoxy-4-(2-<2-octamethyleneimino-piperidine-3-carboxamido>ethyl)benzoic acid.

Melting point 237°–240° C. (from ethanol).

The following compound was obtained in an analogous manner but without conversion into the Na salt with NaOH: 2-Ethoxy-4-(2-<2-hexamethylenimino-pyridine-3-carboxamido>ethyl)benzoic acid.

Melting point 135°–137° C. (from ethanol).

EXAMPLE 2

4-(2-<2-(3,5-Dimethylpiperidino)-pyridine-3-carboxyamido>ethyl)-2-methoxybenzoic acid and Na salt 5.43 g of ethyl 4-(2-<2-chloro-pyridine-3-carboxamido ethyl)-2-methoxybenzoate were reacted with 6.8 g of 3,5-dimethylpiperidine in analogy to Example 1. After hydrolysis of the ester, the 4-(2-<2-(3,5-dimethylpiperidino)-pyridine-3-carboxamido>ethyl)-2-methoxybenzoic acid was obtained, which melted at 73°–75° C. The sodium salt prepared therefrom as in Example 1 melted at 235°–238° C. (from ethanol).

The ethyl 4(2-<2-chloro-pyridine-3-carboxamido>ethyl)-2-methoxybenzoate employed as the starting material was prepared in the following manner:

2-Hydroxy-4-methylbenzoic acid was reacted with $K_2CO_3$ and dimethyl sulfate to give methyl 2-methoxy-4-methybenzoate (boiling point at 0.7 mm=100° C.).

Hydrolysis with 2N sodium hydroxide solution provided 2-methoxy-4-methylbenzoic acid (melting point 103°-104° C.). Bromination to give the 4-bromomethyl compound (melting point 123°-125° C.) and reaction with potassium cyanide provided the 4-cyanomethyl compound (melting point 105°-107° C., from toluene), the catalytic hydrogenation of which with Ra—Ni and reaction with ethanolic hydrochloric acid provided the ethyl 4-(2-aminoethyl)-2-methoxybenzoate hydrochloride (melting point 86°-88° C.).

Reaction of this with 2-chloronicotinic acid, methyl chloroformate and triethylamine provided the ethyl 4-(2-<2-chloro-pyridine-3-carboxamido>ethyl)-2-methoxybenzoate (as an oil).

The following compounds were obtained in a manner analogous to Example 1 or 2: Na salt of 4-(2-<2-heptamethyleneimino-pyridine-3-carboxamido>ethyl)-2-methoxybenzoic acid (plus 1 mole of Na acetate), decomposition point 262°-265° C. (triturated with acetone). Na salt of 2-methoxy-4-(2-<2-octamethyleneimino-pyridine-3-carboxamido>ethyl)benzoic acid as dihydrate, decomposition point 250°-253° C. (triturated with ether).

EXAMPLE 3

Na salt of
4-(2-<2-(3,5-dimethylpiperidino)quinoline-3-carboxamido>ethyl)-2-methoxybenzoic acid 7.1 g of 2-(3,5-dimethylpiperidino)quinoline-3-carboxylic acid, (melting point 56°-58° C., prepared from 2-chloroquinoline-3-carboxylic acid and 3,5-dimethylpiperidine) were dissolved in 25 ml of dimethylformamide. After the addition of 3.82 g of 1-hydroxybenzotriazole, 6.92 ml of triethylamine, 6.18 g of dicyclohexylcarbodiimide and 6.5 g of ethyl 4-(2-aminoethyl)-2-methoxybenzoate hydrochloride (for preparation see Example 2), the mixture was stirred at 40°-50° C. for six hours. The mixture was cooled down, filtered and poured into 300 ml of water. Extraction three times with 100 ml of ethyl acetate each time, which was then washed with sodium bicarbonate solution and water, dried over sodium sulfate and evaporated gave the ethyl 4-(2-<2-(3,5-dimethylpiperidino)quanoline-3-carboxamido>ethyl)-2-methoxybenzoate.

The latter was dissolved in 100 ml of ethanol and, after addition of 25 ml of 2N sodium hydroxide solution, was hydrolyzed. After evaporation in vacuo, the residue was taken up in water and the solution was acidified and extracted with methylene chloride. The carboxylic acid was obtained by evaporation, and this was converted with the equivalent amount of sodium ethylate into the Na salt of 4-(2-<2-(3,5-dimethylpiperidino)-quinoline-3-carboxamido>ethyl)-2-methoxy benzoic acid, which melted at 208°-210° C.

EXAMPLE 4

Na salt of
4-(2-<2-(3,5-dimethylpiperidino)-pyridine-3-carboxamido>-ethyl)-2-methoxybenzoic acid 5.85 g of 2-(3,5-dimethylpiperidino)-nicotinic acid (prepared from 2-chloronicotinic acid and 3,5-dimethylpiperidine) were dissolved in 25 ml of dimethylformamide. After the addition of 10.41 g of 1-hydroxybenzotriazole (32.4%), 6.5 g of 4-(2-aminoethyl)-2-methoxybenzoic acid ethyl ester . hydrochloride, 6.92 ml of triethylamine and 6.18 g of dicyclohexylcarbodiimide the mixture was stirred for 30 minutes at 50° C. and left to stand overnight at room temperature. Dicyclohexylurea obtained was suction-filtered and washed with 25 ml of dimethylformamide. The combined filtrates were poured into 250 ml of ice-water. Extraction three times with 100 ml of ethyl acetate each time, washing of the acetic ester phase with sodium dicarbonate solution and water and concentration in vacuo gave the ethyl 4-(2-<2-(3,5-dimethylpiperidino)-pyridine-3-carboxamido>ethyl)-2-methoxybenzoate.

The latter was dissolved in 25 ml of methanol and, after addition of 40% sodium hydroxide solution, boiled for 6 hours. The solution was evaporated and the residue was dissolved in water. The solution was acidified with glacial acetic and extracted with methylene chloride. The carboxylic acid obtained was converted into the Na salt of 4-(2-<2-(3,5-dimethylpiperidino)-pyridine-3-carboxamido>-ethyl)-2-methoxybenzoic acid (melting point 236°-239° C. from ethanol) with the equivalent quantity of freshly prepared sodium ethylate.

EXAMPLE 5

4-(2-<2-(Cis-3,5-dimethylpiperidino)-pyridine-3-carboxamido>-ethyl)-2-methoxybenzoic acid and the Na salt thereof and
4-(2-<2-(trans-3,5-dimethylpiperidino)-pyridine-3-carboxamido>-ethyl)-2-methoxybenzoic acid and the Na salt thereof The compound obtained according to Example 4 was a cis-trans mixture. Both compounds were obtained by column chromatographic separation. To this purpose, the carboxylic acid was dissolved in the solvent mixture used for the separation and the solution was poured onto a silica gel column. Elution was carried out using 20 ml portions of a mixture of chloroform (20 volume parts), cyclohexane (30 volume parts), glacial acetic acid (5 volume parts) and 90% ethanol (5 volume parts.)

The 4-(2-<2-(cis-3,5-dimethylpiperidino)pyridine-3-carboxamido>ethyl)-2-methoxybenzoic acid obtainable in said manner melted at 128°-130° C. and the Na salt derived therefrom at 256°-258° C.

The 4-(2-<2-(trans-3,4-dimethylpiperidino)pyridine-3-carboxamido>ethyl)-2-methoxybenzoic acid melted at 108°-110° C. and the Na salt derived therefrom at 250°-252° C.

We claim:

1. A salicylic acid derivative of the formula I

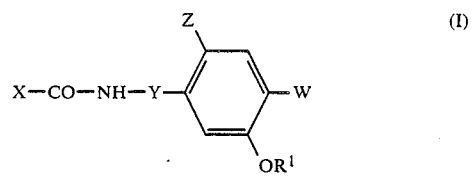

in which W denotes a carboxyl group or an alkoxycarbonyl group having up to 4 carbon atoms in the alkoxy moiety, Z denotes a hydrogen atom or a halogen atom, $R^1$ denotes a hydrogen atom, a $(C_1-C_6)$-alkyl group, a $(C_2-C_6)$-alkenyl group or an alkoxyalkyl group having a total of up to 6 carbon atoms, Y denotes an alkylene radical having 1-3 C atoms, X denotes a pyridine radical of the formula II

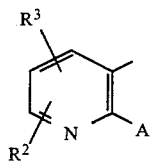 (II)

wherein $R^2$ denotes a hydrogen atom or a halogen atom or an alkyl group having up to 4 C atoms or an alkoxy group having up to 4 C atoms in the alkoxy moiety, $R^3$ denotes a hydrogen atom or an alkyl group having up to 4 C atoms, A denotes a ($C_4$ to $C_8$)-alkyleneimino group, which is unsubstituted or substituted by one or two ($C_1$-$C_4$)-alkyl groups, this group being bonded to the rest of the molecule via the nitrogen atom, or a physiologically tolerated salt with an acid or a base.

2. A compound as claimed in claim 1 wherein Y denotes the $CH_2$—$CH_2$ group, W denotes the carboxyl or alkoxycarbonyl group having up to 2 carbon atoms in the alkoxy moiety, $R^1$ denotes a $C_1$-$C_3$-alkyl group and $R^2$, $R^3$ and Z each denote a hydrogen atom.

3. A medicament for treating diabetes mellitus containing an effective amount of compound according to claim 1 and a suitable pharmaceutically acceptable carrier.

4. A process for treating patients suffering from diabetes mellitus which process comprises administering to a patient an effective quantity of a compound of claim 1.

* * * * *